United States Patent [19]

Richardson et al.

[11] Patent Number: 4,554,286

[45] Date of Patent: Nov. 19, 1985

[54] ANTIFUNGAL 1-TRIAZOLYL-2-ARYL-3-(5-TRIFLUOROMETHYLIMIDAZOL-1-YL)PROPAN-2-OL DERIVATIVES

[75] Inventors: Kenneth Richardson; Peter J. Whittle, both of Canterbury, England

[73] Assignee: Pfizer Inc., New York, N.Y.

[21] Appl. No.: 606,510

[22] Filed: May 3, 1984

[30] Foreign Application Priority Data

May 13, 1983 [GB] United Kingdom ............... 8313235

[51] Int. Cl.$^4$ .................... A01N 43/64; A61K 31/44; C07D 401/14; C07D 403/06
[52] U.S. Cl. .................................. 514/383; 514/341; 546/210; 548/262
[58] Field of Search ....................... 548/262; 546/210; 424/269, 263; 514/383, 341

[56] References Cited

U.S. PATENT DOCUMENTS 4,404,216 9/1983 Richardson ..................... 549/563
4,416,682 11/1983 Worthington ..................... 548/262

FOREIGN PATENT DOCUMENTS 0044605 1/1982 European Pat. Off. ............ 548/262
0122693 10/1984 European Pat. Off. ............ 548/262

*Primary Examiner*—Alton D. Rollins
*Attorney, Agent, or Firm*—Charles J. Knuth; Albert E. Frost; Peter C. Richardson

[57] ABSTRACT

1-Triazolyl-2-aryl-3-(5-trifluoromethylimidazol-1-yl)propan-2-ol derivatives useful in the treatment of fungal infections in humans, animals and plants, and their preparation.

13 Claims, No Drawings

ANTIFUNGAL 1-TRIAZOLYL-2-ARYL-3-(5-TRIFLUOROME-THYLIMIDAZOL-1-YL)PROPAN-2-OL DERIVATIVES

This invention relates to novel triazole derivatives which have antifungal activity and are useful in the treatment of fungal infections in humans and animals.

A number of 1,3-bis-heterocyclyl-propanol derivatives have been previously described as antifungal agents. For example U.K. patent application 2078719A and its counterpart European patent application 0044605 disclose certain 1-triazolyl-2-aryl-3-heterocyclyl-propan-2-ol derivatives as plant and pharmaceutical fungicides and as plant growth regulators. According to the present invention there are provided 1-triazolyl-2-aryl-3-imidazolyl-propan-2-ol derivatives wherein the imidazole ring is substituted in the 5-position with $CF_3$. Such substituted derivatives have unexpectedly improved antifungal activity over the unsubstituted compounds.

Thus, according to the invention, there are provided compounds of the formula:

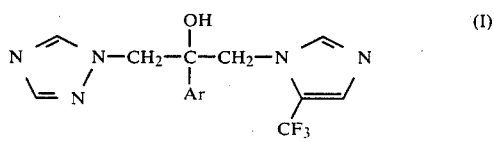

and their O-esters and O-ethers, where Ar is phenyl optionally substituted by 1 to 3 substituents each independently selected from F, Cl, Br, I, trifluoromethyl, $C_1$–$C_4$ alkyl and $C_1$–$C_4$ alkoxy, or Ar is a 5-chloropyrid-2-yl group; and their pharmaceutically acceptable salts.

The invention also provides a pharmaceutical composition comprising a compound of the formula (I) or an O-ester, O-ether or pharmaceutically acceptable salt thereof, together with a pharmaceutically acceptable diluent or carrier.

The invention further provides a compound of the formula (I) or an O-ester, O-ether or pharmaceutically acceptable salt thereof, for use in treating fungal infections in animals, including humans.

When Ar is said optionally substituted phenyl group, it is preferably phenyl substituted by 1 to 3 substitutents, more preferably 1 or 2 substitutents, each independently selected from F, Cl, Br, I and $CF_3$. In particular in this aspect, Ar is 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2,4,6-trifluorophenyl or 4-bromo-2,5-difluorophenyl.

The O-ethers of the compounds of the formula (I) include, for example, the $C_1$–$C_6$ alkyl, ($C_2$–$C_4$ alkenyl)methyl, ($C_2$–$C_4$ alkynyl)methyl, aryl (e.g. phenyl) and aralkyl (e.g. benzyl optionally ring substituted by halo, $C_1$–$C_4$ alkyl or $C_1$–$C_4$ alkoxy) ethers.

The O-esters of the compounds of the formula (I) include, for example, the $C_2$–$C_4$ alkanoyl and aroyl (e.g. benzoyl, optionally substituted by halo, $C_1$–$C_4$ alkyl or $C_1$–$C_4$ alkoxy) esters.

The preferred O-ester is the acetate.

The compounds can be prepared by reacting an oxirane of the formula:

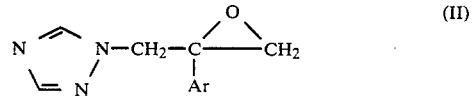

wherein Ar is as previously defined, with an imidazole of formula:

The reaction is preferably performed in the presence of a base, e.g. $K_2CO_3$. Typically the reaction is carried out by heating the reactants together at up to 120° C. in a suitable organic solvent, e.g. dimethylformamide, for up to about 24 hours. The product can be isolated and purified conventionally.

The oxiranes (II) can be obtained by conventional methods, typically from the corresponding ketones (IV):

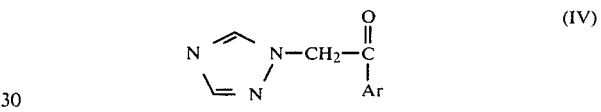

by reaction with dimethyloxosulphonium methylide prepared from trimethylsulphoxonium iodide and either sodium hydride in dimethylsulphoxide or using cetrimide and sodium hydroxide in a mixture of water and toluene.

The reaction using sodium hydride is typically achieved by adding dry powdered trimethylsulphoxonium iodide to a suspension of sodium hydride in dimethylsulfoxide. After stirring for 30 minutes at room temperature, the ketone (IV) is added in an approximately equimolar amount in dimethylsulphoxide. The reaction mixture may be warmed to accelerate the reaction and after several hours at 50°–80° C., the product can be isolated by conventional procedures.

The reaction utilising cetrimide is typically achieved by stirring the ketone (IV), trimethylsulphoxonium iodide and cetrimide vigorously together in a mixture of toluene and sodium hydroxide solution for about an hour at up to about 100° C. The oxirane product can then be isolated by conventional procedures.

The ketones (IV) are either known compounds or can be prepared by procedures analogous to those of the prior art. The preparation of 2-(1H-1,2,4-triazol-1-yl)-2',4'-dichloroacetophenone from 2-bromo-2',4'-dichloroacetophenone, 1,2,4-triazole and potassium carbonate is, for example, described in Example 1 of British Patent Specification No. 1512918, which utilises acetonitrile as the solvent under reflux for 20 hours. We have found that this type of reaction is generally best carried out in acetone at 0°–20° C., when it is generally complete in a shorter period of time, e.g. 4 hours or less The imidazole derivative of formula (III) is a known compound, preparable in accordance with literature precedents.

The O-ethers can be made conventionally, e.g. by treating an alkali metal salt of a compound of the formula (I), e.g. a lithium or sodium salt, with the appropriate halide, e.g. an alkyl, alkenylmethyl, alkynylmethyl or aralkyl halide. O-Esters can be made by treating an alkali metal salt of compound (I) with the appropriate acid chloride, bromide or anhydride.

The compounds of the invention contain an optically active centre and the invention includes both the resolved and unresolved forms.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent. Also included are the alkali metal salts, preparable conventionally.

The compounds of the formula (I) and their O-esters, O-ethers and pharmaceutically acceptable salts are antifungal agents, useful in combatting fungal infections in animals, including humans. For example, they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds is performed by determining the minimum concentration of the test compound which inhibits growth of a particular micro-organism in a suitable medium (m.i.c.). In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Cryptococcus neoformans, Aspergillus fumigatus,* Trichophyton spp; Microsporum spp; *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration; they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful as agricultural fungicides for treating plants and seeds to eradicate or prevent such diseases.

The following Examples illustrate the invention:

EXAMPLE 1

2-(2,4-Dichlorophenyl)-1-(1,2,4-triazol-1-yl)-3-(5-trifluoromethylimidazol-1-yl)-propan-2-ol A mixture of 4-trifluoromethylimidazole (0.7 g, 5 mmole), 2-(2,4-dichlorophenyl)-2-(1,2,4-triazol-1-ylmethyl)-oxirane mesylate salt (1.88 g, 5 mmole) and anhydrous potassium carbonate (2.0 g, 14 mmole) in dry N,N-dimethylformamide (20 ml) was heated at 75°-80° C. for 18 hours. The solvent was evaporated under vacuum and the residue was partitioned between water (20 ml) and methylene chloride (50 ml). The aqueous layer was separated and extracted twice with methylene chloride (30 ml). The organic layers were combined, dried over magnesium sulphate and evaporated to yield the crude product containing the 4- and 5-trifluoromethyl-imidazolyl isomers. The residue was chromatographed on silica eluting with a mixture of hexane, isopropyl alcohol and concentrated ammonium hydroxide (80:20:1.5); fractions containing the minor component were evaporated and the product recrystalised from a mixture of acetone and water to give the desired title compound (0.02 g, 1%), m.p. 190°-192° C.

$C_{14}H_{12}Cl_2F_3N_5O$ requires C, 44.3; H, 3.0; N, 17.2%. Found: C, 44.5; H, 3.1; N, 17.3%.

EXAMPLE 2

Following the procedure of Example 1 but using the appropriate 2-aryl-2-(1,2,4-triazol-1-ylmethyl) oxirane as reactant in place of the 2,4-dichlorophenyl analog used in said Example affords the following compounds:

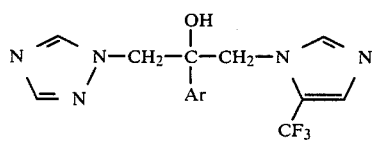

wherein Ar is:
2-chlorophenyl
4-chlorophenyl
4-fluorophenyl
2-fluorophenyl
2,4-difluorophenyl
2-trifluoromethylphenyl phenyl
4-trifluoromethylphenyl
5-chloropyrid-2-yl

EXAMPLE 3

The following illustrate pharmaceutical compositions for the treatment of fungal infections:

(1) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(2) Cream: 2 parts by weight of the compound of Example 1 are dissolved in 10 parts of propylene glycol and mixed into 88 parts of a vanishing cream base.

(3) Pessary: 2 parts by weight of the compound of Example 1 are suspended in 98 parts of a warm liquified suppository base which is poured into moulds and allowed to solidify.

Similarly, pharmaceutical compositions of the compounds of Example 2 are prepared.

PREPARATION 1

Preparation of 2-(2,4-Dichlorophenyl-2-(1H-1,2,4-triazol-1-ylmethyl)-oxirane

Sodium hydride (3.78 g, 0.079 mole as 50% dispersion in oil) was suspended, with stirring, in 20 ml of dry diethyl ether. The ether was then removed by decentation, and the sodium hydride was dried in a stream of dry nitrogen. Dry dimethyl sulphoxide (100 ml) was added followed by 17.34 g (0.079 mole) of dry powdered trimethylsulphoxonium iodide, in portions, over 15 minutes. The resulting mixture was stirred for 30 minutes at room temperature (20° C.). 2-(1H-1,2,4-Triazol-1-yl)-2',4'-dichloro acetophenone (18.33 g, 0.072 mole) as a solution in 50 ml of dry dimethyl sulphoxide was then added. The mixture was heated at 60° C. for 3 hours and allowed to stand at room temperature overnight. The reaction mixture was cooled and quenched in ice. The product was then extracted into ethyl acetate (600 ml). The ethyl acetate layer was separated, dried over magnesium sulphate, and concentrated to give a red gum. Column chromatography of the gum on silica, eluting with ether, gave 6.62 g (34.4%) of the title compound as a gum.

TEST RESULTS

The compound of the Example 1 was tested in vivo by oral administration to mice inoculated with a lethal infection of *Candida albicans* according to the procedures described herein. This was compared with the corresponding compound wherein the imidazole ring is unsubstituted, i.e. the compound 2-(2,4-dichlorophenyl)-1-(imidazol-1-yl)-3-(1,2,4-triazol-1-yl)propan-2-ol. The dose levels providing 50% protection ($PD_{50}$) were as follows:

| EXAMPLE | $PD_{50}$ (mg/kg/p.o.) |
| --- | --- |
| 1 | 0.75 |
| comparative compound | 5.2 |

We claim:

1. A compound of the formula

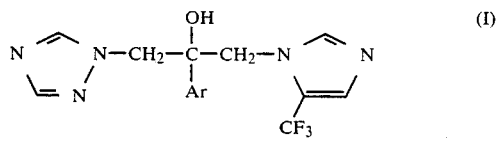

and its $O-C_1-C_6$ alkyl, ($C_2-C_4$ alkenyl)methyl, ($C_2-C_4$ alkynyl)methyl, phenyl and benzyl ethers and $O-C_2-C_4$ alkanoyl and benzoyl esters, where Ar is 5-chloropyrid-2-yl or phenyl optionally substituted by 1 to 2 substituents each independently selected from F, Cl or trifluoromethyl; and pharmaceutically acceptable salts thereof.

2. A compound according to claim 1 wherein Ar is 2-chlorophenyl, 2-fluorophenyl, 4-fluorophenyl, 4-chlorophenyl, 2-trifluoromethylphenyl, 4-trifluoromethylphenyl, 2,4-dichlorophenyl, 2,4-difluorophenyl, phenyl or 5-chloropyrid-2-yl.

3. 2-(2,4-Dichlorophenyl)-1-(1,2,4-triazol-1-yl)-3-(5-trifluoromethylimidazol-1-yl)-propan-2-ol, the compound according to claim 2 wherein Ar is 2,4-dichlorophenyl.

4. 2-(2,4-Difluorophenyl)-1-(1,2,4-triazol-1-yl)-3-(5-trifluoromethylimidazol-1-yl)-propan-2-ol, the compound according to claim 2 wherein Ar is 2,4-difluorophenyl.

5. 2-(4-Chlorophenyl)-1-(1,2,4-triazol-1-yl)-3-(5-trifluoromethylimidazol-1-yl)-propan-2-ol, the compound according to claim 2 wherein Ar is 4-chlorophenyl.

6. 2-(4-Fluorophenyl)-1-(1,2,4-triazol-1-yl)-3-(5-trifluoromethylimidazol-1-yl)-propan-2-ol, the compound according to claim 2 wherein Ar is 4-fluorophenyl.

7. A pharmaceutical composition comprising an antifungally effective amount of a compound according to claim 1, or a pharmaceutically acceptable salt thereof, together with a pharmaceutically acceptable diluent or carrier.

8. A pharmaceutical composition comprising an antifungally effective amount of a compound according to claim 2, or a pharmaceutically acceptable salt thereof, together with a pharmaceutically acceptable diluent or carrier.

9. A fungicidal composition for agricultural use, comprising an antifungally effective amount of a compound according to claim 1, or an agriculturally acceptable salt thereof, together with an agriculturally acceptable diluent or carrier.

10. A method of treating a fungal infection in a mammal which comprises treating said mammal with an antifungally effective amount of a compound according to claim 1, or a pharmaceutically acceptable salt thereof.

11. A method of treating a fungal infection in a mammal which comprises treating said mammal with an antifungally effective amount of a compound according to claim 2 or a pharmaceutically acceptable salt thereof.

12. The method of treating a fungal infection in a mammal which comprises treating said mammal with an antifungally effective amount of the compound according to claim 3.

13. A method of treating a plant or seed having a fungal infection, which comprises treating said plant or seed, or the locus of said plant, with an antifungally effective amount of a compound according to claim 1, or with an agriculturally acceptable salt thereof.

* * * * *